US009303172B2

(12) United States Patent
Iftime et al.

(10) Patent No.: US 9,303,172 B2
(45) Date of Patent: *Apr. 5, 2016

(54) SPREADABLE INK COMPOSITION AND METHOD OF PREDICTING WHETHER INK COMPOSITION WILL HAVE ACCEPTABLE SPREADING PERFORMANCE

(71) Applicant: XEROX CORPORATION, Norwalk, CT (US)

(72) Inventors: Gabriel Iftime, Mississauga (CA); Gordon Sisler, St. Catharines (CA); Biby Esther Abraham, Mississauga (CA); Nathan M. Bamsey, Burlington (CA); Edward Graham Zwartz, Mississauga (CA)

(73) Assignee: XEROX CORPORATION, Norwalk, CT (US)

( * ) Notice: Subject to any disclaimer, the term of this patent is extended or adjusted under 35 U.S.C. 154(b) by 124 days.

This patent is subject to a terminal disclaimer.

(21) Appl. No.: 14/068,594

(22) Filed: Oct. 31, 2013

(65) Prior Publication Data

US 2015/0114255 A1 Apr. 30, 2015

(51) Int. Cl.
 C09D 11/02 (2014.01)
 C09D 11/34 (2014.01)
 G01N 11/00 (2006.01)
(52) U.S. Cl.
 CPC .............. *C09D 11/02* (2013.01); *C09D 11/34* (2013.01); *G01N 11/00* (2013.01); *G01N 2011/002* (2013.01); *G01N 2203/0075* (2013.01); *G01N 2203/0092* (2013.01)

(58) Field of Classification Search
 CPC ...................................................... C09D 11/34
 See application file for complete search history.

(56) References Cited

U.S. PATENT DOCUMENTS

| 6,471,758 | B1 * | 10/2002 | Kelderman et al. | 106/31.29 |
| 8,287,632 | B1 * | 10/2012 | Morimitsu et al. | 106/31.29 |
| 8,328,924 | B2 * | 12/2012 | Morimitsu et al. | 106/31.29 |
| 8,591,640 | B1 * | 11/2013 | Goredema et al. | 106/31.29 |
| 8,647,423 | B2 * | 2/2014 | Iftime et al. | 106/31.29 |
| 8,741,040 | B2 * | 6/2014 | Morimitsu et al. | 106/31.29 |
| 8,741,043 | B2 * | 6/2014 | Goredema et al. | 106/31.29 |
| 8,747,535 | B1 * | 6/2014 | Chopra et al. | 106/31.29 |
| 8,753,441 | B2 * | 6/2014 | Vanbesien et al. | 106/31.29 |
| 8,758,494 | B2 * | 6/2014 | Vanbesien et al. | 106/31.29 |
| 8,784,547 | B2 * | 7/2014 | Vanbesien et al. | 106/31.29 |
| 8,882,897 | B2 * | 11/2014 | Morimitsu et al. | 106/31.61 |
| 8,961,673 | B2 * | 2/2015 | Chopra et al. | 106/31.61 |

(Continued)

OTHER PUBLICATIONS

Naveen Chopra, "Phase Change Ink Compositions Comprising Crystalline Diurethanes and Derivatives Thereof", U.S. Appl. No. 13/456,619, filed Apr. 26, 2012.

(Continued)

*Primary Examiner* — Veronica F Faison
(74) *Attorney, Agent, or Firm* — MH2 Technology Law Group LLP

(57) ABSTRACT

A phase change ink composition is disclosed. The phase change ink composition comprises a crystalline component and an amorphous component. At a temperature ranging from about 40° C. to about 80° C., the phase change ink simultaneously exhibits (i) a static force ranging from about 2 N to about 4.5 N, and (ii) a storage modulus ranging from about 300 MPa to about 700 Mpa. The crystalline component is not a wax. A method of predicting spreading performance of a phase change ink is also disclosed.

19 Claims, 6 Drawing Sheets

(56) References Cited

U.S. PATENT DOCUMENTS

| | | | |
|---|---|---|---|
| 2003/0225187 A1* | 12/2003 | Everhardus et al. | 523/160 |
| 2012/0272860 A1* | 11/2012 | Belelie et al. | 106/31.13 |
| 2012/0272864 A1* | 11/2012 | Morimitsu et al. | 106/31.61 |
| 2012/0274700 A1* | 11/2012 | Belelie et al. | 347/20 |
| 2013/0284051 A1* | 10/2013 | Iftime et al. | 106/31.13 |
| 2013/0284052 A1* | 10/2013 | Vanbesien et al. | 106/31.13 |
| 2013/0284055 A1* | 10/2013 | Belelie et al. | 106/31.28 |
| 2013/0284056 A1* | 10/2013 | Chopra et al. | 106/31.61 |
| 2013/0284057 A1* | 10/2013 | Belelie et al. | 106/31.61 |
| 2013/0284058 A1* | 10/2013 | Morimitsu et al. | 106/31.61 |
| 2013/0284059 A1* | 10/2013 | Chopra et al. | 106/31.61 |
| 2013/0284060 A1* | 10/2013 | Morimitsu et al. | 106/31.61 |
| 2013/0284061 A1* | 10/2013 | Morimitsu et al. | 106/31.61 |

OTHER PUBLICATIONS

Kentaro Morimitsu, "Phase Change Ink Compositions Comprising Aromatic Ethers", U.S. Appl. No. 13/456,916, filed Apr. 26, 2012.

Jennifer L. Belelie, "Phase Change Inks Comprising Organic Pigments", U.S. Appl. No. 13/456,805, filed Apr. 26, 2012.

Naveen Chopra, "Phase Change Ink Compositions Comprising Diurethanes as Amorphous Materials", U.S. Appl. No. 13/457,068, filed Apr. 26, 2012.

Kentaro Morimitsu, "Phase Change Inks Comprising Crystalline Amides", U.S. Appl. No. 13/457,221, filed Apr. 26, 2012.

Gariel Iftime, "Phase Change Inks Comprising Fatty Acids", U.S. Appl. No. 131456,722, filed Apr. 26, 2012.

Kentaro Morimitsu, "Phase Change Inks Comprising Aromatic Diester Crystalline Compounds", U.S. Appl. No. 13/457,300, filed Apr. 26, 2012.

\* cited by examiner

FIG. 4

Coded Coefficients

| Y-HAT MODEL | | FLW | | | |
|---|---|---|---|---|---|
| FACTOR | NAME | Coeff | P(2 TAIL) | TOL | ACTIVE |
| CONST | | 0.08022 | 0.0000 | | |
| A | Tdrum | -0.00926 | 0.0042 | 0.6162 | X |
| B | STATIC FORCE | -0.06734 | 0.0000 | 0.0395 | X |
| C | STORAGE MODULUS | 0.05521 | 0.0000 | 0.0354 | X |
| AA | | -0.01513 | 0.0071 | 0.7302 | X |
| AB | | 0.01847 | 0.0048 | 0.6334 | X |
| BB | | -0.07410 | 0.0001 | 0.0367 | X |
| BC | | 0.20597 | 0.0000 | 0.0091 | X |
| CC | | -0.10174 | 0.0000 | 0.0281 | X |
| R² | | 0.8164 | | | |
| ADJ R² | | 0.7757 | | | |
| STD ERROR | | 0.0070 | | | |
| F | | 20.0163 | | | |
| SIG F | | 0.0000 | | | |
| F LOF | | NA | | | |
| SIG F LOF | | NA | | | |
| SOURCE | | SS | df | MS | |
| REGRESSION | | 0.0 | 8 | 0.0 | |
| ERROR | | 0.0 | 36 | 0.0 | |
| ERROR PURE | | NA | 0 | NA | |
| ERROR LOF | | NA | 0 | NA | |
| TOTAL | | 0.0 | 44 | | |

Uncoded (Actual) Coefficients

| Y-HAT MODEL | | FLW | | | |
|---|---|---|---|---|---|
| FACTOR | NAME | Coeff | P(2 TAIL) | TOL | ACTIVE |
| CONST | | 0.16422 | | | |
| A | Tdrum | 0.00112 | 0.0115 | | X |
| B | STATIC FORCE | -0.07205 | 0.0033 | | X |
| C | STORAGE MODULUS | 0.0002891 | 0.0082 | | X |
| AA | | -0.0000242 | 0.0107 | | X |
| AB | | 0.0002050 | 0.0140 | | X |
| BB | | -0.00570 | 0.0013 | | X |
| BC | | 0.0001498 | 0.0002 | | X |
| CC | | -0.0000007 | 0.0008 | | X |
| R² | | 0.8164 | | | |
| ADJ R² | | 0.7757 | | | |
| STD ERROR | | 0.0070 | | | |
| F | | 20.0163 | | | |
| SIG F | | 0.0000 | | | |
| F LOF | | NA | | | |
| SIG F LOF | | NA | | | |
| SOURCE | | SS | df | MS | |
| REGRESSION | | 0.0 | 8 | 0.0 | |
| ERROR | | 0.0 | 36 | 0.0 | |
| ERROR PURE | | NA | 0 | NA | |
| ERROR LOF | | NA | 0 | NA | |
| TOTAL | | 0.0 | 44 | | |

SPREADABLE INK COMPOSITION AND METHOD OF PREDICTING WHETHER INK COMPOSITION WILL HAVE ACCEPTABLE SPREADING PERFORMANCE

DETAILED DESCRIPTION

1. Field of the Disclosure

The present disclosure is directed to phase change ink compositions and a method of determining whether phase change ink compositions will have acceptable spreading performance.

2. Background

Many features of Xerox phase change inks have been improved in recent time. Extensive experimental work enabled identification of ways to predict and improve key ink properties such as: scratch resistance, fold offset, and solidification rate.

However, one of the most difficult to predict properties is the ink spread ability during the print process. In direct to paper print process, spreading is performed as the last step by fusing the printed paper under pressure and heat. A large number of inks have been tested in the past and it turned out that inks with good spreading properties are not common place. In fact, only very few inks other than Xerox 8560 ink, which is a wax based phase change ink, could be spread to specifications. When it comes to spreading, most of the work has been essentially based on a trial and error approach. The problem is that there is poor understanding of what the actual physical properties are which make a phase change ink spread well.

Novel inks that provide good spread ability, as well as a novel technique for predicting the spread ability of inks, would be welcome advances in the art.

SUMMARY

An embodiment of the present disclosure is directed to a phase change ink. The phase change ink comprises a crystalline component and an amorphous component. At a temperature ranging from about 40° C. to about 80° C., the phase change ink simultaneously exhibits (i) a static force ranging from about 2 N to about 4.5 N, and (ii) a storage modulus ranging from about 300 MPa to about 700 Mpa. The crystalline component is not a wax.

Another embodiment of the present disclosure is directed to a method of predicting spreading performance of a phase change ink. The method comprises providing a desired static force range and a desired storage modulus range. A sample of the phase change ink is provided. A static force of the phase change ink at a first temperature, and a storage modulus of the phase change ink at the first temperature, are both determined. If the determined static force is within the desired static force range and the determined storage modulus is within the desired storage modulus range, than it can be predicted that the phase change ink will provide an acceptable spreading performance. If the determined static force is not within the desired static force range or the determined storage modulus is not within the desired storage modulus range, that it is not predicted that the phase change ink will provide an acceptable spreading performance.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrates embodiments of the present teachings and together with the description, serve to explain the principles of the present teachings.

FIG. 4. shows DOE Regression output data, as set forth in an example of the present disclosure.

Figure 1:
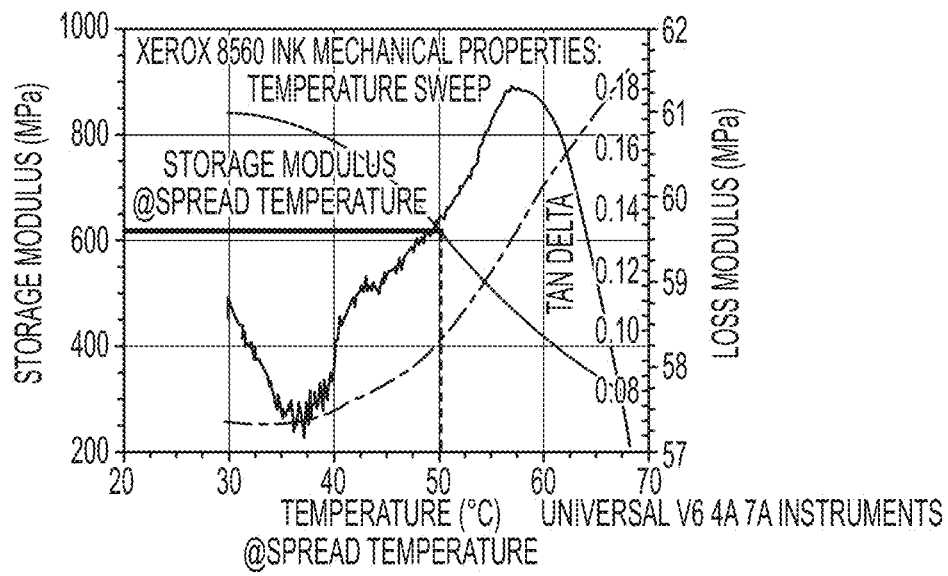
FIG. 1 shows complex modulus test results as a function of spread temperature for Xerox 8560 ink, according to an example of the present disclosure.

It should be noted that some details of the figure have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. In the drawings, like reference numerals have been used throughout to designate identical elements. In the following description, reference is made to the accompanying drawing that forms a part thereof, and in which is shown by way of illustration a specific exemplary embodiment in which the present teachings may be practiced. The following description is, therefore, merely exemplary.

Phase Change Ink Compositions

The inventors of the present disclosure have discovered that phase change ink compositions with certain mechanical properties can exhibit desired spreading characteristics. These mechanical properties, which include static force and storage modulus, can be used as a predictor for spread performance of phase change ink compositions.

An embodiment of the present disclosure is directed to a phase change ink with a static force and storage modulus within specified ranges. The phase change ink comprises: a crystalline component and an amorphous component. At a temperature ranging from about 40° C. to about 80° C. the phase change ink simultaneously exhibits, for example, (i) a static force ranging from about 2 N to about 4.5 N, and (ii) a storage modulus ranging from about 300 MPa to about 700 Mpa.

Any suitable crystalline component can be employed in the compositions of the present disclosure. Examples of suitable crystalline components are discussed in the compositions described below. In an embodiment, the crystalline component of the ink is not a wax. In another embodiment, the phase change ink composition as a whole does not include a wax. The crystalline component can have a molecular weight that is less than, for example, 2000 g/mol. In an embodiment, the crystalline materials component has a viscosity ranging from about 2 to about 50 centipoise at a temperature of 140° C.

Any suitable amorphous component can be employed in the compositions of the present disclosure. Examples of suitable amorphous components are discussed in the compositions described below. In an embodiment, the amorphous materials can be low molecular (small molecules) materials having a molecular weight that is less than 1000 g/mol, such as a molecular weight that is less than 900 g/mol, or less than 800 g/mol.

The various individual crystalline and amorphous components taught in the present disclosure can be used in any suitable combination to form phase change ink compositions. Other suitable ingredients, such as pigments and/or fatty acids, which are discussed in more detail below, can also be included in the in the phase change ink compositions of the present disclosure. One of ordinary skill in the art would readily be able to determine suitable combinations of the various crystalline and amorphous components and/or other ingredients, given the teachings provided herein.

Examples of phase change inks can include those comprising a crystalline component that is a diurethane having a formula of

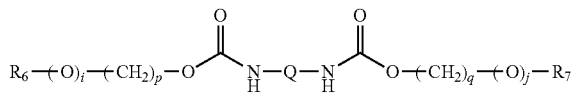

where Q is alkanediyl; each $R_6$ and $R_7$ is independently phenyl or cyclohexyl optionally substituted with one or more alkyl; i is 0 or 1; j is 0 or 1; p is 1 to 4; and q is 1 to 4. The phase change ink can include an amorphous component comprising an ester of tartaric acid of Formula I or an ester of citric acid of Formula II:

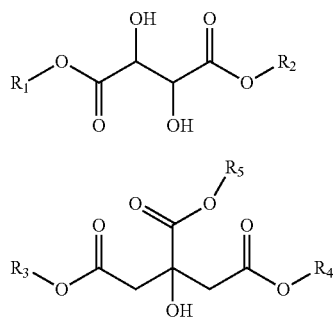

wherein each $R_1$, $R_2$, $R_3$, $R_4$ and $R_5$ is independently an alkyl group, wherein the alkyl can be straight, branched or cyclic, saturated or unsaturated, substituted or unsubstituted, having from about 1 to about 40 carbon atoms, or a substituted or unsubstituted aromatic or heteroaromatic group, and mixtures thereof. These phase change ink can crystallize in less than 15 seconds. Examples of such inks are disclosed in U.S. patent application Ser. No. 13/456619, filed Apr. 26, 2012, the disclosure of which is hereby incorporated by reference in its entirety.

In an embodiment, the phase change ink can include a crystalline component that is an aromatic ether having the following structure:

wherein $R_6$ and $R_7$ is independently selected from the group consisting of (i) an alkyl group, which can be a linear or branched, cyclic or acyclic, substituted or unsubstituted, saturated or unsaturated, alkyl group, and wherein heteroatoms may optionally be present in the alkyl group, in embodiments, having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group, in embodiments, having from about 4 to about 40 carbon atoms; and (iii) an aromatic group, which can be a substituted or unsubstituted aromatic group, wherein the substituent can be a linear, branched, cyclic or acyclic alkyl group and wherein heteroatoms may optionally be present in the aromatic group, having from about 3 to about 40 carbon atoms; and mixtures thereof, provided that at least one of $R_6$ and $R_7$ is an aromatic group; and p is 0 or 1. The phase change ink can include an amorphous component comprising an ester of tartaric acid of Formula I or an ester of citric acid of Formula II:

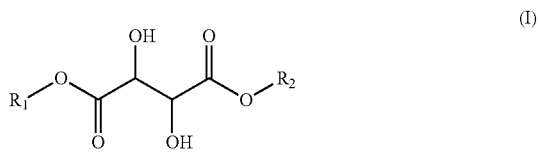

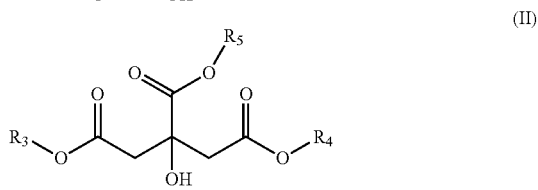

wherein each $R_1$, $R_2$, $R_3$, $R_4$ and $R_5$ is independently an alkyl group, wherein the alkyl can be straight, branched or cyclic, saturated or unsaturated, substituted or unsubstituted, having from about 1 to about 40 carbon atoms, or a substituted or unsubstituted aromatic or heteroaromatic group, and mixtures thereof. In an embodiment, the phase change ink crystallizes in less than 15 seconds. Examples of such inks are disclosed in U.S. patent application Ser. No. 13/456916, filed Apr. 26, 2012, the disclosure of which is hereby incorporated by reference in its entirety.

In an embodiment, the phase change ink comprises an organic pigment, where the addition of an organic pigment to the composition made of crystalline and amorphous components results in acceleration of the crystallization of the ink when cooling from the molten state. Thus, the phase change ink crystallizes faster from the liquid state than the same composition without an organic pigment. One or a plurality of organic pigments can be employed. Examples of suitable organic pigments include Carbon Black, Pigment Blue 15, Pigment Blue 15:1, Pigment Blue 15:2, Pigment Blue 15:3, Pigment Blue 15:4, Pigment Blue 15:6, Pigment Blue 1, Pigment Blue 10, Pigment Blue 14, Pigment Blue 60, Pigment Blue 61, Pigment Yellow 1, Pigment Yellow 3, Pigment Yellow 12, Pigment Yellow 13, Pigment Yellow 14, Pigment Yellow 17, Pigment Yellow 24, Pigment Yellow 55, Pigment Yellow 62, Pigment Yellow 63, Pigment Yellow 65, Pigment Yellow 73, Pigment Yellow 74, Pigment Yellow 81, Pigment Yellow 83, Pigment Yellow 93, Pigment Yellow 95, Pigment Yellow 97, Pigment Yellow 110, Pigment Yellow 111, Pigment Yellow 123, Pigment Yellow 126, Pigment Yellow 127, Pigment Yellow 139, Pigment Yellow 147, Pigment Yellow 150, Pigment Yellow 151, Pigment Yellow 154, Pigment Yellow 155, Pigment Yellow 168, Pigment Yellow 170, Pigment Yellow 174, Pigment Yellow 175, Pigment Yellow 176, Pigment Yellow 179, Pigment Yellow 180, Pigment Yellow 183, Pigment Yellow 185, Pigment Yellow 188, Pigment Yellow 191, Pigment Yellow 194, Pigment Yellow 214, Pigment Red 2, Pigment Red 3, Pigment Red 4, Pigment Red 5, Pigment Red 8, Pigment Red 9, Pigment Red 12, Pigment Red 13, Pigment Red 21, Pigment Red 22, Pigment Red 23, Pigment Red 31, Pigment Red 32, Pigment Red 48:1, Pigment Red 48:2, Pigment Red 48:3, Pigment Red 48:4, Pigment Red 49:1, Pigment Red 49:2, Pigment Red 52:1, Pigment Red 52:2, Pigment Red 53:1, Pigment Red 53:3, Pigment Red 57:1, Pigment Red 63:1, Pigment Red 81, Pigment Red 112, Pigment Red 122, Pigment Red 123, Pigment Red 144, Pigment Red 146, Pigment Red 149, Pigment Red 166, Pigment Red 169, Pigment Red 170, Pigment Red 171, Pigment Red 175, Pigment Red 176, Pigment Red 177, Pigment Red 178, Pigment Red 179, Pigment Red 184, Pigment Red 185, Pigment Red 188, Pigment Red 189, Pigment Red 202, Pigment Red 208, Pigment Red 210, Pigment Red 224. Pigment Red 242, Pigment Red 245, Pigment Red 254, Pigment Red 266, Pigment Red 268, Pigment Red 269, Pigment Orange 5, Pigment Orange 13, Pigment Orange 16, Pigment Orange 34, Pigment Orange 36, Pigment Orange 63, Pigment Violet 1, Pigment Violet 2, Pigment Violet 3, Pigment Violet 19, Pigment Violet 23, Pigment Violet 27, Pigment Green 7, Pigment Green 36, all listed in the Color Index publication by the Society of Dyers and Colourists and the American Association of Textile Chemists and Colorists. Mixtures of any of the above pigments can be employed. The amorphous compound can comprise a first ester of tartaric acid of Formula I or a first ester of citric acid of Formula II:

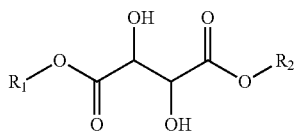
(I)

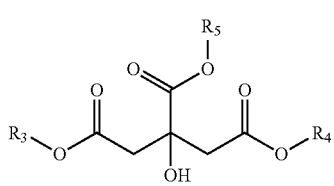
(II)

wherein each $R_1$, $R_2$, $R_3$, $R_4$ and $R_5$ is independently an alkyl group, wherein the alkyl is straight, branched or cyclic, saturated or unsaturated, substituted or unsubstituted, having from about 1 to about 40 carbon atoms, or an substituted or unsubstituted aromatic or heteroaromatic group. The crystalline compound comprises a second ester of tartaric acid of Formula III:

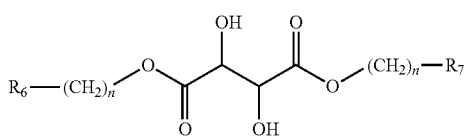
(III)

wherein each $R_6$ and $R_7$ is independently an aryl or a heteroaryl optionally substituted with a lower alkyl and alkoxy, each n is independently 0 to 3. Examples of inks that include an organic pigment are disclosed in U.S. patent application Ser. No. 13/456805, filed Apr. 26, 2012, the disclosure of which is hereby incorporated by reference in its entirety.

In an embodiment, the phase change ink can include and amorphous compound having a formula of:

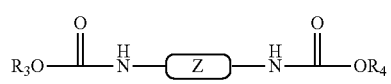

wherein Z is selected from the group consisting of

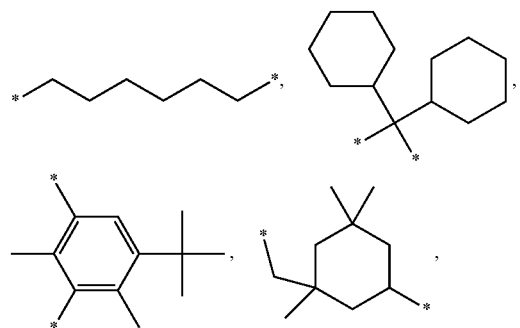

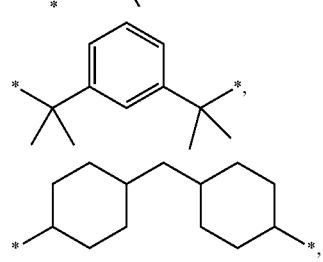

, and

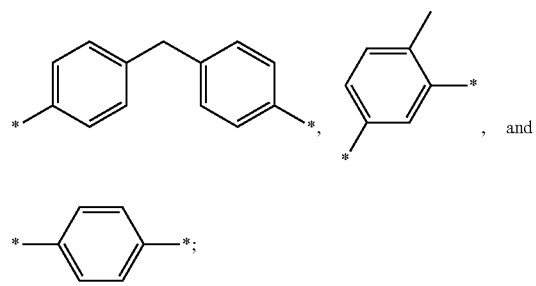

;

wherein each $R_3$ and $R_4$ is i) an alkyl group wherein the alkyl can be linear or branched having from about 1 to about 8 carbon atoms, or ii) an aryl group; with the proviso that when Z is —$(CH_2)_6$—, both $R_3$ and $R_4$ are not —$(CH_2)_n$—$C_6H_5$, and wherein n=0-4. In an embodiment these phase change ink crystallizes in less than 15 seconds. Examples of such inks are disclosed in U.S. patent application Ser. No. 13/457068, filed Apr. 26, 2012, the disclosure of which is hereby incorporated by reference in its entirety.

In an embodiment, the phase change inks of the present disclosure can include a crystalline compound that is an amide having a formula of:

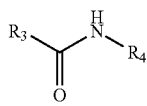
(II)

wherein each $R_3$ and $R_4$ is independently selected from the group consisting of (i) an alkyl group, which can be a linear or branched, cyclic or acyclic, substituted or unsubstituted, saturated or unsaturated, alkyl group, and wherein heteroatoms may optionally be present in the alkyl group having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group having from about 4 to about 40 carbon atoms; and (iii) an aromatic group, which can be a substituted or unsubstituted aromatic group wherein the substituent can be a linear, branched, cyclic or acyclic alkyl group and, wherein heteroatoms may optionally be present in the aromatic group having from about 3 to about 40 carbon atoms, and mixtures thereof. Examples of amorphous compounds that can employed in the phase change ink include esters of tartaric acid of Formula

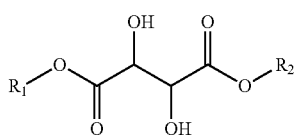
(I)

wherein each $R_1$ and $R_2$ is independently an alkyl group, wherein the alkyl can be straight, branched or cyclic, saturated or unsaturated, substituted or unsubstituted, having from about 1 to about 40 carbon atoms, or an substituted or unsubstituted aromatic or heteroaromatic group, and mixtures thereof. In an embodiment, the phase change ink crystallizes in less than 15 seconds. Examples of these inks are disclosed in U.S. patent application Ser. No. 13/457,221, filed Apr. 26, 2012, the disclosure of which is hereby incorporated by reference in its entirety.

In an embodiment, the phase change ink of the present disclosure can comprise a fatty acid, wherein the phase change ink crystallizes faster from the liquid state than the same composition without the fatty acid. Fatty acids may contain carbon chains of about 12 to about 28 carbons, about 16 to about 24 carbons, or about 18 to about 22 carbons. The fatty acid may be saturated or unsaturated. Specific non-limiting examples of fatty acids include, but are not limited to, palmitic acid (hexadecanoic acid), palmitoleic acid (9-hexadecenoic acid), stearic acid (octadecanoic acid), oleic acid (9-octadecenoic acid), ricinoleic acid (12-hydroxy-9-octadecenoic acid), vaccenic acid (11-octadecenoic acid), linoleic acid (9,12-octadecadienoic acid), alpha-linolenic acid (9,12,15-octadecatrienoic acid), gamma-linolenic acid (6,9,12-octadecatrienoic acid), arachidic acid (eicosanoic acid), gadoleic acid (9-eicosenoic acid), arachidonic acid (5,8,11,14-eicosatetraenoic acid), erucic acid (13-docosenoic acid), and mixtures thereof. In certain embodiments, the fatty acid is stearic acid. In certain embodiments, the fatty acid is behenic acid. The percentage by weight of the fatty acid in an ink composition of the invention can range from about 0.1% to about 25%, about 1% to about 15%, or about 2% to about 10%. Examples of amorphous compounds that can be employed with the fatty acids include a first ester of tartaric acid of Formula I or a first ester of citric acid of Formula II:

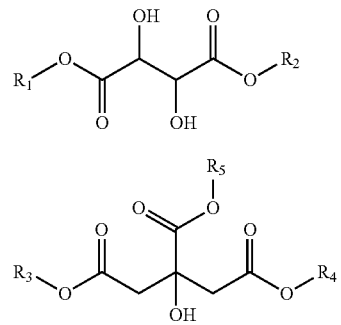

wherein each $R_1$, $R_2$, $R_3$, $R_4$ and $R_5$ is independently an alkyl group, wherein the alkyl can be straight, branched or cyclic, saturated or unsaturated, substituted or unsubstituted, having from about 1 to about 40 carbon atoms. Examples of crystalline compounds that can be employed comprise a second ester of tartaric acid of Formula III:

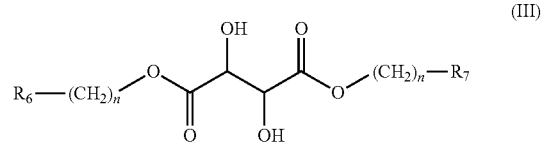
(III)

wherein each $R_6$ and $R_7$ is independently an aryl or a heteroaryl optionally substituted with a lower alkyl and alkoxy, each n is independently 0 to 3. These inks are disclosed in U.S. patent application Ser. No. 13/456722, filed Apr. 26, 2012, the disclosure of which is hereby incorporated by reference in its entirety.

In an embodiment, the phase change inks of the present disclosure can include a crystalline compound comprising the following structure:

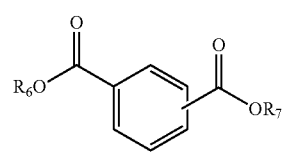
(III)

wherein $R_6$ and $R_7$ can be the same or different, and wherein $R_6$ and $R_7$ each, independently of the other is selected from the group consisting of (i) an alkyl group, which can be a linear or branched, cyclic or acyclic, substituted or unsubstituted, saturated or unsaturated, alkyl group, and wherein heteroatoms may optionally be present in the alkyl group having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group having from about 4 to about 40 carbon atoms; and (iii) an aromatic group, which can be a substituted or unsubstituted aromatic group wherein the substituent can be a linear, branched, cyclic or acyclic alkyl group and, wherein heteroatoms may optionally be present in the aromatic group having from about 3 to about 40 carbon atoms, and mixtures thereof. In an embodiment, the phase change ink can crystallize in less than 15 seconds. Examples of such inks are disclosed in U.S. patent application Ser. No. 13/457300, filed Apr. 26, 2012, the disclosure of which is hereby incorporated by reference in its entirety.

In an embodiment, the colorants employed in the inks of the present disclosure are chosen from a dye, a pigment or mixtures thereof. Any dye or pigment may be chosen, provided that it is capable of being dispersed or dissolved in the ink carrier and is compatible with the other ink components. In an embodiment, pigments other than the organic pigments already listed above can be employed.

Any other ingredients suitable for use in phase change inks can also optionally be included in the compositions of the present disclosure. One of ordinary skill in the art would readily be able to determine other ingredients that can be employed.

Method of Predicting Spreading Performance

Another embodiment of the present disclosure is directed to a method of predicting spreading performance of a phase change ink. Spreading performance can be characterized by whether a desired final line width for printed ink specimens is achieved at printer spreading temperatures for a particular printing process. For example, in experimental work performed with example phase change ink compositions of the present disclosure that had an initial line width of about 50 microns, an acceptable desired final line width achieved after spreading was defined to include line widths ranging from about 100 to about 120 microns. This range is not intended to be limiting, and a desired final line width will vary depending on the ink being employed, the substrate onto which the ink is printed, and the particular spreading equipment being used, among other factors.

Dynamic Mechanical Analysis (DMA) measures viscoelastic properties of a material as it is deformed under controlled stress or strain. The properties measured by DMA in this disclosure were the static force and storage modulus.

Figure 7:
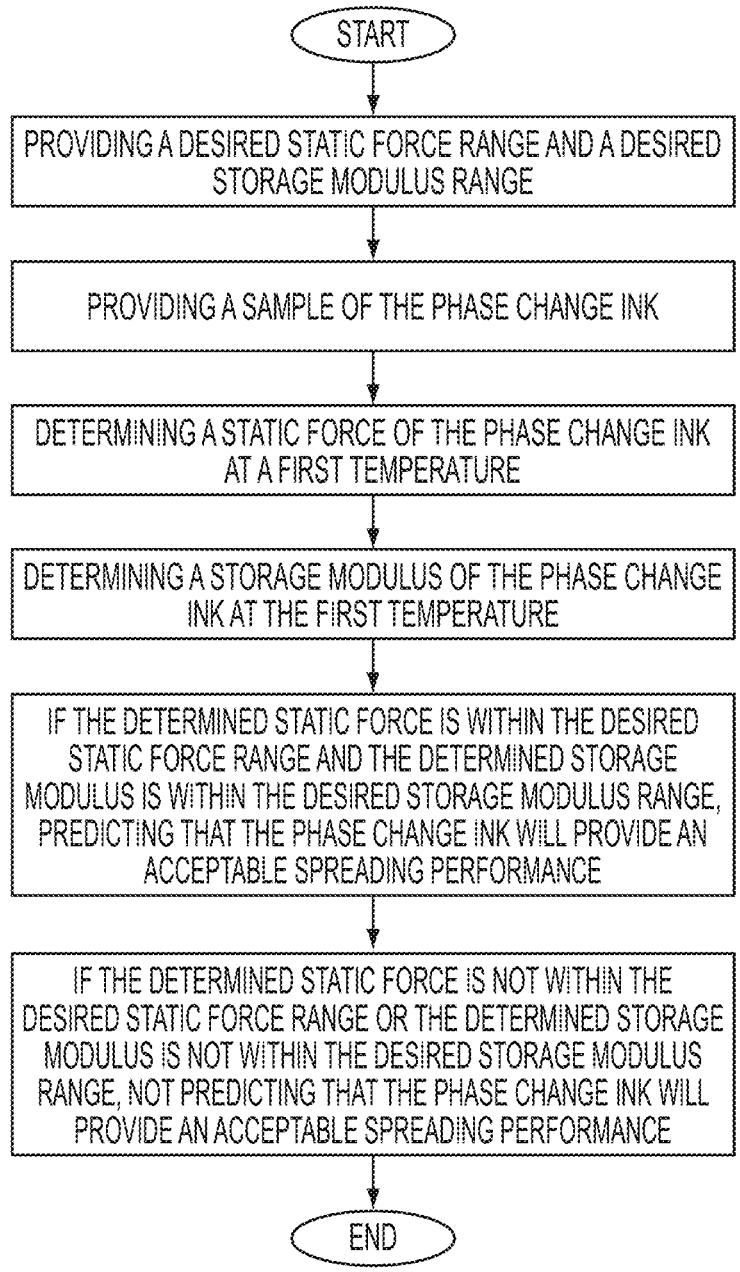
FIG. 7 illustrated a method of predicting spreading performance of a phase change ink, according to an embodiment of the present disclosure.

As shown in FIG. 7, the method of the present disclosure comprises providing a desired static force range and a desired storage modulus range that can be used to predict whether acceptable spreading performance specifications will be met at ink spreading temperatures for a phase change ink composition being tested. The desired static force and storage modulus ranges used can be determined experimentally, such as by using a regression analysis technique, as was employed in the example discussed later on below.

In an embodiment, experimentally determined storage modulus ranges for predicting spreading performance have been found to range from about 300 MPa to about 700 Mpa, such as about 300 MPa to about 600 MPa, or about 400 MPa to about 600 MPa. Experimentally determined static force ranges for predicting spreading performance have been found to range from about 2 N to about 4.5 N, such as about 2 N to about 4 N, or about 2.5 N to about 4 N.

After the predetermined storage modulus and static force ranges are determined for a specified ink spreading temperature range, a sample of a phase change ink is provided. In order to predict the spreading characteristics of the ink sample, testing of the sample can be performed to determine a static force and a storage modulus at the ink spreading temperature.

If the determined static force of the ink sample is within the desired static force range and the determined storage modulus is within the desired storage modulus range, then it can be predicted that the phase change ink will provide an acceptable spreading performance (e.g., a desired line width is achieved). If, on the other hand, it is determined that the static force is not within the desired static force range or the determined storage modulus is not within the desired storage modulus range, than either no prediction is made, or it may be predicted that the phase change ink will not provide an acceptable spreading performance.

Determining a storage modulus for the ink sample can be done using any suitable technique. In an embodiment, determining a storage modulus of the phase change ink comprises measuring the storage modulus of the ink sample. Any suitable method for measuring storage modulus can be employed. Suitable methods are well known in the art.

One example of such a test for determining storage modulus is the Complex Modulus Test. This test involves applying a sinusoidal deformation to the sample and gives sample response as a function of temperature increased at a constant rate. For example, this test was employed to determine storage modulus for the materials in the Examples below, where the strain was selected in the linear viscoelastic region for the material tested and the frequency was 1 Hz. This test gives the measure of Storage Modulus, Loss Modulus and Tan Delta. FIG. 1 shows a representative example of measured storage modulus properties for Xerox 8560 ink, which is a wax based phase change ink. The Storage Modulus represents elastic portion of the complex modulus of the material (Stiffness). It is a measure of the energy stored by the material. In other words, the storage modulus characterizes the stiffness of the material at a given temperature. The Loss Modulus represents the viscous portion of the material. It gives the measure of energy dissipation (as heat) by material. The tan delta is the ratio between the two Moduli and represents the phase lag in elastic response due to energy dissipation in viscoelastic materials.

Determining a static force of the phase change ink comprises measuring the static force of the ink. Any suitable technique for measuring the static force can be used. Suitable techniques are well known in the art.

Figure 2:
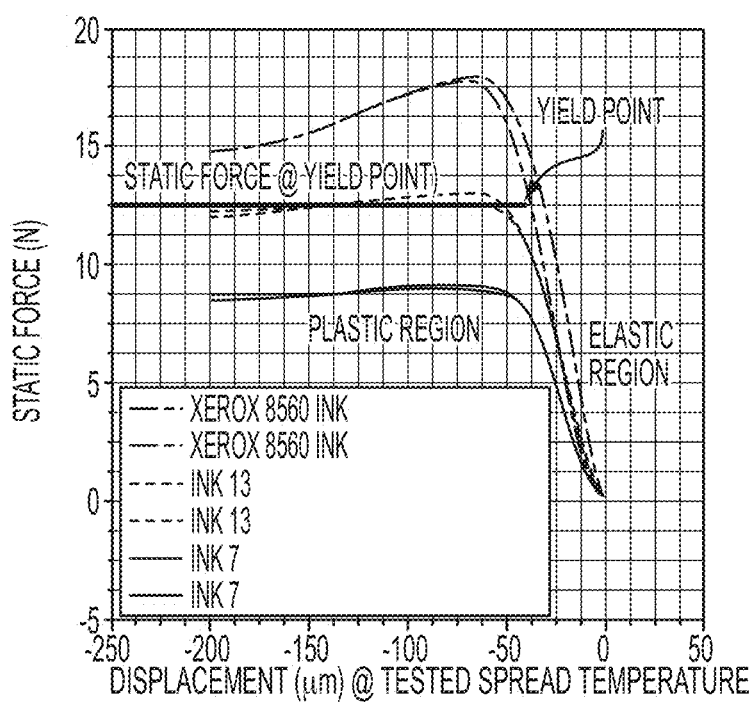
FIG. 2 illustrates examples of static force results for the Xerox 8560 ink, proprietary ink #13 and proprietary ink #7, according to an example of the present disclosure.

For example, testing employed to determine static force for materials in the Examples below employed a penetration clamp used to measure static force applied to phase-change ink samples during an indentation test conducted at constant penetration depth rate and a specified temperature. Phase-change ink samples tested in this manner exhibited a clear demarcation of static force, corresponding to yield stress, indicating their elasto-plastic nature. The measured static force is proportional to the hardness of the material. FIG. 2 shows a representative example of measured static force. The reported static force at the yield point is a function of the tested ink materials and for the same material, a function of the temperature. The actual measured numbers for the static force are also a function of the penetration rate. For the purpose of consistency, all the static force reported here were measured at a displacement rate of 10 µm/min. The Static force at yield point was entered into the DOE model.

The methods of the present disclosure for predicting spread ability of phase change inks can provide certain benefits. For example, relatively small samples of inks can be employed to predict spread ability, allowing target spread performance to be more easy achieved.

EXAMPLES

In an effort to understand the fundamental physical properties required for phase change inks with good spreading, a study was initiated to identify a possible relationship between the measurable mechanical properties of the ink at the spreading temperature and the spreading performance of actual printed samples with the same ink. Based on correlations of available historical inks spread data, it was discovered that there is an optimal range of mechanical property specifications within which phase change inks spread well. Systematic Design of Experiments (DOE) approach provided the actual range for these specifications, which would be otherwise impossible to predict. Industrial DOE is described for example in "Understanding Industrial Designed Experiments," S. R. Schmidt and R. G. Launsby, Air Academy Press, Colorado Springs, Colo., $4^{th}$ edition, 2005, ISBN 1-880156-03-2.

Dynamic Mechanical Analysis (DMA) Sample Preparation Procedure

Experiments have shown that measured mechanical properties can change as a function of changing the sample preparation procedure. Therefore in the interest of getting as close as possible to what happens to a molten droplet of ink when placed onto the paper, the fastest possible cooling rate achievable was attempted with the mold. The preferred procedure consisted in melting the test ink in the mold followed by ice cooling (fastest achievable cooling rate). Attempts to faster cooling rates by using dry ice and even liquid nitrogen resulted actually in slower cooling rate of the sample to the room temperature. This is because of extremely fast evaporation of these cooling agents when in contact with the hot mold.

Phase-change ink samples satisfying the dual cantilever sample geometry used in this testing were prepared using a mold. The mold provided samples having the following dimensions:

$L \times W \times H = 60$ mm $\times 12.8$ mm $\times 3.2$ mm.

Spread Test Description

Inks were printed using a Phaser 8860 modified to print direct-to-paper. Single pixel lines were printed on Xerox Digital Color Elite Gloss 120 gsm coated paper at a fixed resolution of 563×400 dpi (dots per inch) and a drop mass of 25 ng±2 ng at a range of drum temperatures (substrate temperature). Optimal spread temperature was determined for each ink tested. The optimal spread temperature was the highest drum temperature possible without offset of halftones onto the roller.

Figure 3:
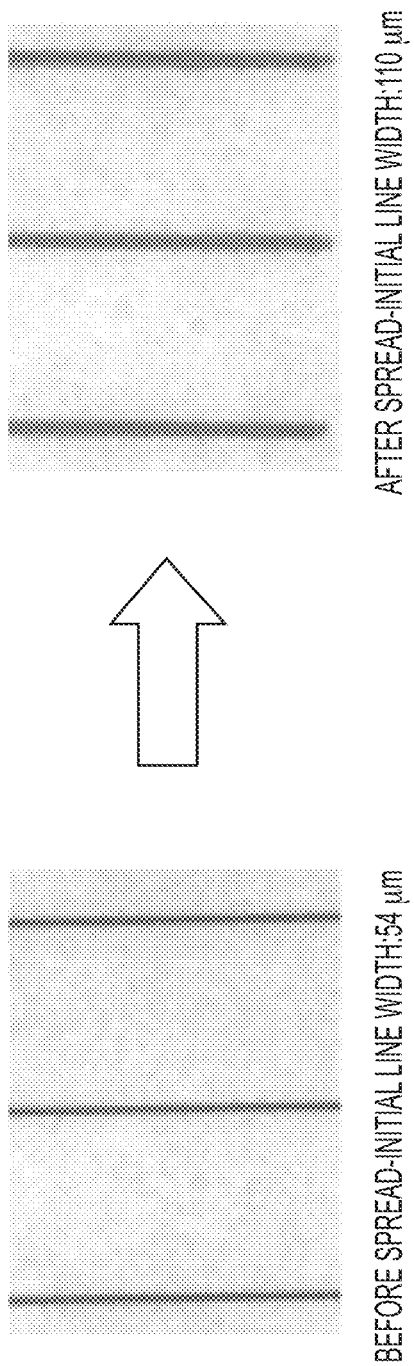
FIG. 3 shows an example of lines printed with the Xerox 8560 ink, before and after spreading to final line width of 110 microns.

Once the optimal spread temperature was found for an ink, line width was measured with a QEA PIAS-II Image Analysis System and QEA software on an un-spread print. The prints were then spread in a Phaser 8860 at the optimal spread temperature and measured for final line width. FIG. 3 shows example images of single pixel lines and measured line width before and after spread.

Experimental Results and Model Building

Experimental data was collected for a set of 45 entries. This consisted of a set of 14 inks tested for spreading at various temperatures. All the data is shown in the Table 1. The table includes: the spreading temperature, the storage modulus and the static force measured at the tested spreading temperature and the print (or drum) temperature, i.e. the temperature of the substrate at the printing stage. Extensive correlation attempts were carried out in order to investigate the possible contribution of other potentially relevant factors such as: the crystallization rate, additional mechanical properties such as tan delta and storage modulus. In all the DOE models they were not significant factors, and therefore were excluded from the DOE model. The model disclosed here is the simplest model which accounts reasonably well for the experimental results.

The DOE model is a historical data regression model type having as factors (Xs):
Drum temperature (printing temperature)
Spread temperature (experimentally programmed)
Static Force at the given spreading temperature (experimentally measured by DMA)
Elastic Modulus at the given spreading temperature (experimentally measured by DMA)
The model had one output (Y) which is the final line width after spreading a printed line at the spreading temperature.

TABLE 1

Input table for DOE Model.

| # | Ink id | Drum Temperature [° C.] | Spread Temperature [° C.] | Static Force [N] | Storage Modulus {MPa} | Final line width [mm] |
|---|---|---|---|---|---|---|
| 1 | Xerox 8560 ink | 50 | 45 | 5.94 | 725 | 0.090 |
| 2 | Xerox 8560 ink | 50 | 50 | 3.70 | 622 | 0.117 |
| 3 | Xerox 8560 ink | 50 | 55 | 3.06 | 515 | 0.131 |
| 4 | Xerox 8560 ink | 50 | 60 | 2.13 | 414 | 0.138 |
| 5 | Ink 2 | 40 | 50 | 6.85 | 800 | 0.067 |
| 6 | Ink 2 | 40 | 55 | 5.30 | 745 | 0.076 |
| 7 | Ink 2 | 40 | 60 | 3.75 | 700 | 0.096 |
| 8 | Ink 3 | 40 | 50 | 6.32 | 780 | 0.072 |
| 9 | Ink 3 | 40 | 55 | 5.22 | 750 | 0.086 |
| 10 | Ink 3 | 40 | 60 | 4.10 | 700 | 0.108 |
| 11 | Ink 4 | 30 | 50 | 7.25 | 965 | 0.075 |
| 12 | Ink 4 | 40 | 50 | 7.25 | 965 | 0.078 |
| 13 | Ink 4 | 50 | 50 | 7.25 | 965 | 0.082 |
| 14 | Ink 4 | 60 | 50 | 7.25 | 965 | 0.078 |
| 15 | Ink 4 | 70 | 50 | 7.25 | 965 | 0.076 |
| 16 | Ink 4 | 80 | 50 | 7.25 | 965 | 0.073 |
| 17 | Ink 4 | 50 | 60 | 7.35 | 877 | 0.083 |
| 18 | Ink 4 | 50 | 70 | 6.10 | 811 | 0.084 |
| 19 | Ink 4 | 50 | 80 | 4.05 | 747 | 0.095 |
| 20 | Ink 5 | 40 | 55 | 6.91 | 1018 | 0.079 |
| 21 | Ink 5 | 50 | 55 | 6.91 | 1018 | 0.076 |
| 22 | Ink 5 | 60 | 55 | 6.91 | 1018 | 0.082 |
| 23 | Ink 5 | 70 | 55 | 6.91 | 1018 | 0.079 |
| 24 | Ink 6 | 40 | 55 | 3.91 | 725 | 0.099 |
| 25 | Ink 6 | 60 | 55 | 3.91 | 725 | 0.088 |
| 26 | Ink 6 | 60 | 50 | 4.77 | 782 | 0.084 |
| 27 | Ink 6 | 60 | 60 | 3.03 | 669 | 0.085 |
| 28 | Ink 7 | 40 | 40 | 5.70 | 765 | 0.100 |
| 29 | Ink 7 | 60 | 40 | 5.70 | 765 | 0.09 |
| 30 | Ink 8 | 40 | 45 | 5.78 | 880 | 0.088 |
| 31 | Ink 8 | 60 | 45 | 5.78 | 880 | 0.083 |
| 32 | Ink 8 | 60 | 50 | 4.51 | 817 | 0.081 |
| 33 | Ink 8 | 40 | 50 | 5.48 | 725 | 0.091 |
| 34 | Ink 8 | 60 | 50 | 5.48 | 725 | 0.081 |
| 35 | Ink 8 | 60 | 55 | 4.36 | 670 | 0.089 |
| 36 | Ink 9 | 40 | 50 | 9.34 | 1003 | 0.068 |
| 37 | Ink 9 | 50 | 50 | 9.34 | 1003 | 0.076 |
| 38 | Ink 9 | 60 | 50 | 9.34 | 1003 | 0.078 |
| 39 | Ink 9 | 70 | 50 | 9.34 | 1003 | 0.078 |
| 40 | Ink 9 | 50 | 60 | 6.61 | 990 | 0.087 |
| 41 | Ink 10 | 45 | 50 | 2.83 | 336.233 | 0.095 |
| 42 | Ink 10 | 50 | 50 | 2.83 | 336.233 | 0.092 |
| 43 | Ink 10 | 55 | 50 | 2.83 | 336.233 | 0.100 |
| 44 | Ink 11 | 40 | 55 | 6.92 | 1099 | 0.076 |
| 45 | Ink 11 | 70 | 55 | 6.92 | 1099 | 0.069 |

Regression Results

Figure 5:
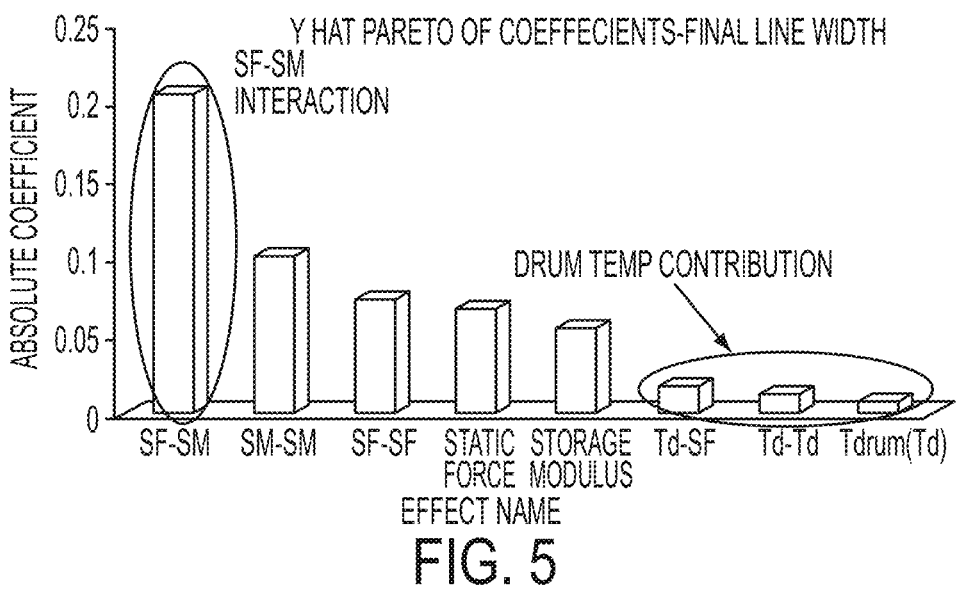
FIG. 5 shows a Pareto graph of uncoded regression coefficients (absolute) illustrating the strong interaction between Static Force and Storage Modulus factors for predicting the spread final line width, as described in the examples of the present disclosure.

The regression output is shown below in FIG. 4 with coded coefficients and with the uncoded (actual) coefficients. The table with the uncoded coefficients describes the mathematical model accounting for the data. Key observations regarding the regression output included the following:

a. The regression output showed notably a $R^2=0.8164$ and an $AdjR^2=0.776$. Given the complexity of spreading process the correlation is significant.

b. The spread temperature was not considered a significant factor in the model, and so was eliminated.

c. The Tolerance for Drum temperature was acceptable (>0.5) i.e. was an independent variable. However the Tolerance for the mechanical properties (Storage Modulus and the Static Force) was very low. In other words, storage modulus and static force were confounding variables.
d. Static Force and Storage Modulus were very significant factors. However, the most important factor was the interaction between these two factors. This is shown in FIG. 5.
e. The strong interaction between Static Force and Storage Modulus was unpredictable without modeling work, which was the key enabler for identifying mechanical property specification claims.

Basically, it was found using the regression model that any given ink the Static Force and Storage Modulus are set (known) once the Spread Temperature is set. Therefore even if the spread temperature does not appear in the model explicitly, it is actually included indirectly (confounded) with the Static Force and the Storage Modulus input data.

Model cconfirmation runs were performed either with inks included in the model but spread or printed at different temperatures that were not entries in model building (Ink 9 and Ink 10), or with inks which were not at all part of the model (Ink 12). Comparison between the actual final line widths (FLW) and the predicted values shows that the model was confirmed (Table 2).

| Ink | Drum Temperature | Spread Temperature | Static Force | Storage Modulus | Actual FLW | Predicted FLW | +/−3 sigma |
|---|---|---|---|---|---|---|---|
| Ink 9 | 50 | 55 | 7.98 | 990 | 0.085 | 0.088 | 0.067-0.109 |
| Ink 10 | 40 | 50 | 2.83 | 336 | 0.096 | 0.104 | 0.084-0.126 |
| Ink 12 | 40 | 50 | 5.33 | 845 | 0.084 | 0.087 | 0.067-0.108 |
| Ink 12 | 60 | 50 | 5.33 | 845 | 0.082 | 0.083 | 0.062-0.104 |

Figure 6:
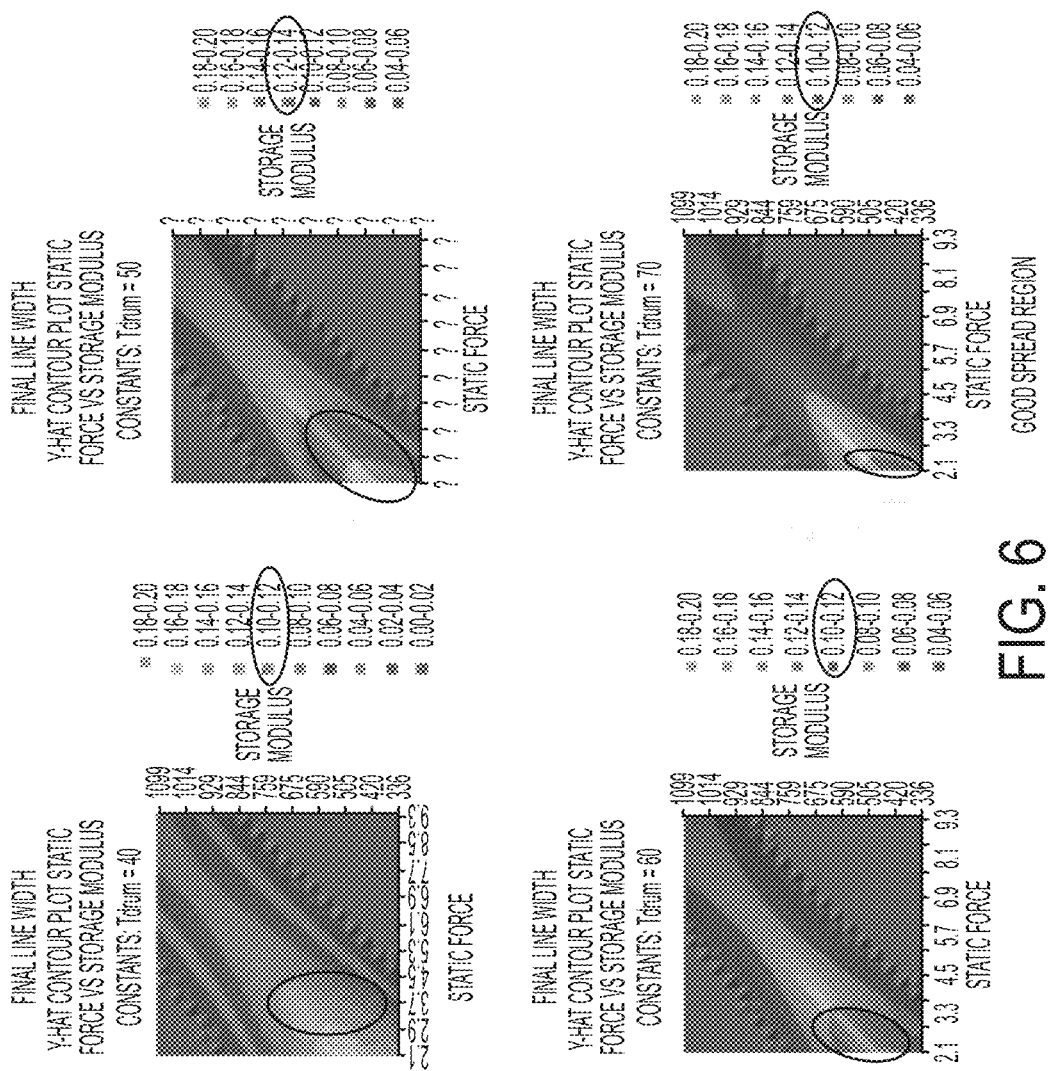
FIG. 6 shows a graph identifying regions with good spreading as a function of static force and storage modulus based on an example DOE model developed, according to an embodiment of the present disclosure.

The contour plots in FIG. 6 were traced by keeping drum temperature fixed at different temperatures over the range where it was practical to print phase change inks. The regions circled in red are the regions where the static force and storage modulus need to be simultaneously in order to provide spreading to a final line width between about 0.100 mm and about 0.120 mm. One can see some variation of the ideal region depending on the printing drum temperature.

Based on the graphs of FIG. 6, one can conclude that an ink will spread well (100 to 120 microns) if it is spread at a temperature wherein the ranges for mechanical properties at the spreading temperature (comprised from about 40° C. to about 80° C.) are as follows:

Static Force: from about 2N to about 4.5 N.
Storage Modulus: from about 300 MPa to about 700 MPa For purposed of this example, good spreading was defined as the ink spreading to about 100 microns to about 120 microns at the spread temperature. However, good spreading can be defined differently if desired.

It is believed that this is the first time specifications for mechanical properties have been identified as a predictor for spread performance of phase change ink. The mathematical model can work for any phase change ink typically composed of crystalline and amorphous components, including both wax based inks and non-waxed based inks.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:
1. A phase change ink, comprising:
a crystalline component; and
an amorphous component;
wherein at a temperature ranging from about 40° C. to about 80° C. the phase change ink simultaneously exhibits (i) a static force ranging from about 2 N to about 4.5 N, and (ii) a storage modulus ranging from about 300 MPa to about 700 MPa,
wherein the crystalline component is not a wax and is selected from the group consisting of:
a) a diurethane having a formula of

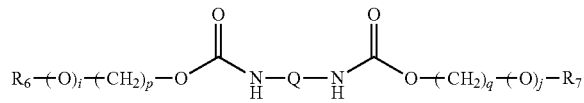

where Q is alkanediyl; each $R_6$ and $R_7$ is independently phenyl or cyclohexyl optionally substituted with one or more alkyl; i is 0 or 1; j is 0 or 1; p is 1 to 4; and g is 1 to 4;
b) an aromatic ether having the following structure:

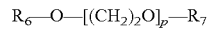

(III)

wherein $R_6$ and $R_7$ is independently selected from the group consisting of (i) an alkyl group, which can be a linear or branched, cyclic or acyclic, substituted or unsubstituted, saturated or unsaturated, alkyl group, and wherein heteroatoms may optionally be present in the alkyl group, in embodiments, having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group, in embodiments, having from about 4 to about 40 carbon atoms; and (iii) an aromatic group, which can be a substituted or unsubstituted aromatic group, wherein the substituent can be a linear, branched, cyclic or acyclic alkyl group and wherein heteroatoms may optionally be present in the aromatic group, having from about 3 to about 40 carbon atoms; and mixtures thereof, provided that at least one of $R_6$ and $R_7$ is an aromatic group; and p is 0 or 1;

c) an amide having a formula of:

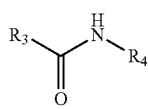

(II)

wherein each of $R_3$ and $R_4$ is independently selected from the group consisting of (i) an alkyl group, which can be a linear or branched, cyclic or acyclic, substituted or unsubstituted, saturated or unsaturated, alkyl group, and wherein heteroatoms may optionally be present in the alkyl group having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group having from about 4 to about 40 carbon atoms; and (iii) an aromatic group, which can be a substituted or unsubstituted aromatic group wherein the substituent can be a linear, branched, cyclic or acyclic alkyl group and, wherein heteroatoms may optionally be present in the aromatic group having from about 3 to about 40 carbon atoms, and mixtures thereof; and d) a compound of the following structure:

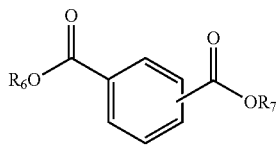

(III)

wherein $R_6$ and $R_7$ can be the same or different, and wherein $R_6$ and $R_7$ each, independently of the other is selected from the group consisting of (i) an alkyl group, which can be a linear or branched, cyclic or acyclic, substituted or unsubstituted, saturated or unsaturated, alkyl group, and wherein heteroatoms may optionally be present in the alkyl group having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group having from about 4 to about 40 carbon atoms; and (iii) an aromatic group, which can be a substituted or unsubstituted aromatic group wherein the substituent can be a linear, branched, cyclic or acyclic alkyl group and, wherein heteroatoms may optionally be present in the aromatic group having from about 3 to about 40 carbon atoms, and mixtures thereof.

2. The phase change ink of claim 1, wherein the amorphous component has a molecular weight that is less than 1000 g/mol.

3. The phase change ink of claim 1, wherein the crystalline component has a molecular weight that is less than 2000 g/mol.

4. The phase change ink of claim 1, wherein the crystalline component has a viscosity ranging from about 2 to about 50 centipoise at a temperature of 140° C.

5. The phase change ink of claim 1, wherein:
the crystalline component is the diurethane having a formula of

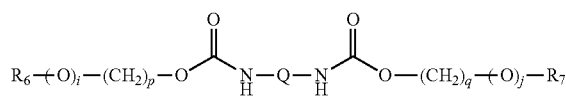

where Q is alkanediyl; each $R_6$ and $R_7$ is independently phenyl or cyclohexyl optionally substituted with one or more alkyl; i is 0 or 1; j is 0 or 1; p is 1 to 4; and q is 1 to 4; and wherein the phase change ink crystallizes in less than 15 seconds.

6. The phase change ink of claim 1, wherein:
the crystalline component is the aromatic ether having the following structure:

$R_6$—O—[(CH$_2$)$_2$O]$_p$—$R_7$ (III)

wherein $R_6$ and $R_7$ is independently selected from the group consisting of (i) an alkyl group, which can be a linear or branched, cyclic or acyclic, substituted or unsubstituted, saturated or unsaturated, alkyl group, and wherein heteroatoms may optionally be present in the alkyl group, in embodiments, having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group, in embodiments, having from about 4 to about 40 carbon atoms; and (iii) an aromatic group, which can be a substituted or unsubstituted aromatic group, wherein the substituent can be a linear, branched, cyclic or acyclic alkyl group and wherein heteroatoms may optionally be present in the aromatic group, having from about 3 to about 40 carbon atoms; and mixtures thereof, provided that at least one of $R_6$ and $R_7$ is an aromatic group; and p is 0 or 1;

wherein the phase change ink crystallizes in less than 15 seconds.

7. The phase change ink of claim 1, wherein the amorphous component comprises an ester of tartaric acid of Formula I or an ester of citric acid of Formula II

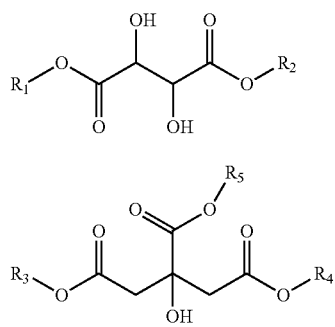

wherein each $R_1$, $R_2$, $R_3$, $R_4$ and $R_5$ is independently an alkyl group, wherein the alkyl can be straight, branched or cyclic, saturated or unsaturated, substituted or unsubstituted, having from about 1 to about 40 carbon atoms, or a substituted or unsubstituted aromatic or heteroaromatic group, and mixtures thereof.

8. The phase change ink of claim 1, further comprising:

an organic pigment; and wherein the phase change ink crystallizes faster from the liquid state than the same composition without an organic pigment.

9. The phase change ink of claim 1, wherein:

the amorphous compound is an amorphous diurethane compound having a formula of:

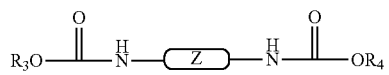

wherein Z is selected from the group consisting of

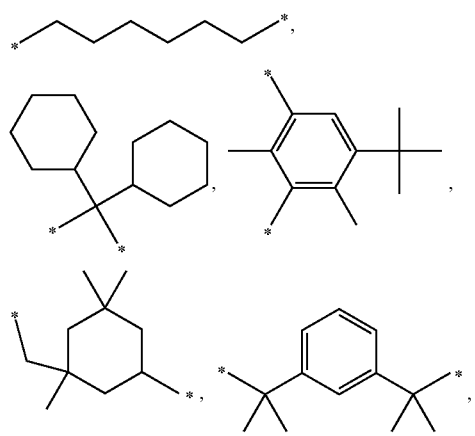

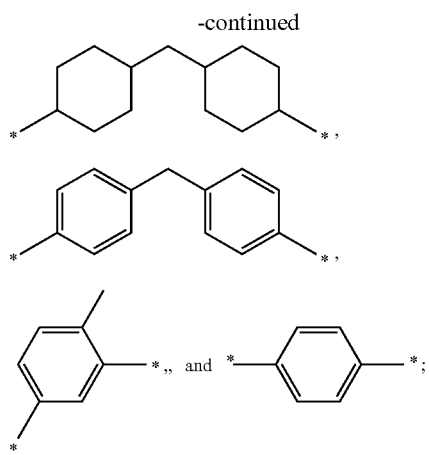

wherein each $R_3$ and $R_4$ is i) an alkyl group wherein the alkyl can be linear or branched having from about 1 to about 8 carbon atoms, or ii) an aryl group; with the proviso that when Z is —$(CH_2)_6$—, both $R_3$ and $R_4$ are not —$(CH_2)_n$—$C_6H_5$ wherein n=0–4; and wherein the phase change ink crystallizes in less than 15 seconds.

10. The phase change ink of claim 1, wherein:

the crystalline compound is the amide having a formula of:

wherein each $R_3$ and $R_4$ is independently selected from the group consisting of (i) an alkyl group, which can be a linear or branched, cyclic or acyclic, substituted or unsubstituted, saturated or unsaturated, alkyl group, and wherein heteroatoms may optionally be present in the alkyl group having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group having from about 4 to about 40 carbon atoms; and (iii) an aromatic group, which can be a substituted or unsubstituted aromatic group wherein the substituent can be a linear, branched, cyclic or acyclic alkyl group and, wherein heteroatoms may optionally be present in the aromatic group having from about 3 to about 40 carbon atoms, and mixtures thereof; and wherein the phase change ink crystallizes in less than 15 seconds.

11. The phase change ink of claim 10, wherein the amorphous compound comprises an ester of tartaric acid of Formula I

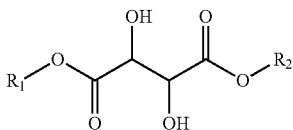

(I)

wherein each R₁ and R₂ is independently an alkyl group, wherein the alkyl can be straight, branched or cyclic, saturated or unsaturated, substituted or unsubstituted, having from about 1 to about 40 carbon atoms, or an substituted or unsubstituted aromatic or heteroaromatic group, and mixtures thereof.

12. A phase change ink, comprising:
a fatty acid;
a crystalline component; and
an amorphous component;
wherein at a temperature ranging from about 40° C. to about 80° C. the phase change ink simultaneously exhibits (i) a static force ranging from about 2 N to about 4.5 N, and (ii) a storage modulus ranging from about 300 MPa to about 700 MPa,
wherein the crystalline component is not a wax; and
wherein the phase change ink crystallizes faster from the liquid state than the same composition without the fatty acid.

13. The phase change ink of claim 12, wherein the amorphous compound comprises a first ester of tartaric acid of Formula I or a first ester of citric acid of Formula II

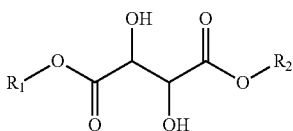

(I)

(II)

wherein each R₁, R₂, R₃, R₄ and R₅ is independently an alkyl group, wherein the alkyl can be straight, branched or cyclic, saturated or unsaturated, substituted or unsubstituted, having from about 1 to about 40 carbon atoms; and
the crystalline compound comprises a second ester of tartaric acid of Formula III:

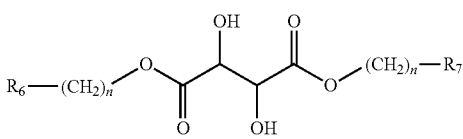

(III)

wherein each R₆ and R₇ is independently an aryl or a heteroaryl optionally substituted with a lower alkyl and alkoxy, each n is independently 0 to 3.

14. The phase change ink of claim 1, wherein:
the crystalline compound is the compound of structure:

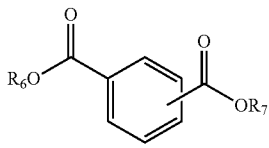

(III)

wherein R₆ and R₇ can be the same or different, and wherein R₆ and R₇ each, independently of the other is selected from the group consisting of (i) an alkyl group, which can be a linear or branched, cyclic or acyclic, substituted or unsubstituted, saturated or unsaturated, alkyl group, and wherein heteroatoms may optionally be present in the alkyl group having from about 1 to about 40 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group having from about 4 to about 40 carbon atoms; and (iii) an aromatic group, which can be a substituted or unsubstituted aromatic group wherein the substituent can be a linear, branched, cyclic or acyclic alkyl group and, wherein heteroatoms may optionally be present in the aromatic group having from about 3 to about 40 carbon atoms, and mixtures thereof;
wherein the phase change ink crystallizes in less than 15 seconds.

15. A method of predicting spreading performance of a phase change ink, the method comprising:
providing a desired static force range and a desired storage modulus range;
providing a sample of the phase change ink;
determining a static force of the phase change ink at a first temperature;
determining a storage modulus of the phase change ink at the first temperature;
if the determined static force is within the desired static force range and the determined storage modulus is within the desired storage modulus range, predicting that the phase change ink will provide an acceptable spreading performance; and
if the determined static force is not within the desired static force range or the determined storage modulus is not within the desired storage modulus range, not predicting that the phase change ink will provide an acceptable spreading performance.

16. The method of claim 15, wherein the desired static force range is about 2 N to about 4.5 N.

17. The method of claim 15, wherein the desired storage modulus range is about 300 MPa to about 700 MPa.

18. The method of claim 15, wherein determining a static force of the phase change ink comprises measuring the static force of the ink.

19. The method of claim 15, wherein determining a storage modulus of the phase change ink comprises measuring the static force of the ink.

* * * * *